United States Patent [19]
Henrick et al.

[11] 4,093,622
[45] June 6, 1978

[54] PYRIDINE ESTERS OF CYCLOPROPANE-CARBOXYLIC ACID

[75] Inventors: Clive A. Henrick; Gerardus B. Staal, both of Palo Alto, Calif.

[73] Assignee: Zoecon Corporation, Palo Alto, Calif.

[21] Appl. No.: 708,825

[22] Filed: Jul. 26, 1976

Related U.S. Application Data

[60] Division of Ser. No. 578,837, May 19, 1975, abandoned, which is a continuation-in-part of Ser. No. 418,595, Nov. 23, 1973, abandoned.

[51] Int. Cl.$^2$ .......................................... C07D 213/51
[52] U.S. Cl. ................................ 260/295 R; 544/353; 544/399; 544/283; 544/237; 544/235; 544/335; 544/408; 544/336; 544/224; 544/239; 544/406; 260/287 R; 260/293.65; 260/295.5 R; 260/302 A; 260/307 H; 260/326.2; 260/329 R; 260/329 S; 260/330.5; 260/332.2 A; 260/346.22; 260/347.2; 260/347.4; 260/347.5; 548/325
[58] Field of Search .................................... 260/295 R

[56] References Cited
U.S. PATENT DOCUMENTS
3,438,993   4/1969   Wilbert et al. ...................... 260/295

*Primary Examiner*—Donald G. Daus
*Assistant Examiner*—Lisa Jones
*Attorney, Agent, or Firm*—Donald W. Erickson

[57] ABSTRACT

Heterocyclic organic esters and thioesters characterized by the presence of one or two cyclopropane moieties, synthesis thereof, and compositions thereof for the control of mites and ticks.

2 Claims, No Drawings

PYRIDINE ESTERS OF CYCLOPROPANE-CARBOXYLIC ACID

This is a division of Ser. No. 578,837, filed May 19, 1975, now abandoned, which is a continuation-in-part of Ser. No. 418,595, filed Nov. 23, 1973, now abandoned.

This invention relates to novel compounds, synthesis thereof, compositions thereof, and the control of mites and ticks.

The compounds of the present invention are effective for the control of mites and especially spider mites.. Spider mites are plant feeders and cause serious damage to orchard trees, field crops, greenhouse plants and other vegetation. They feed on the foliage of fruit of plants and trees and attack a variety of plants and trees due to their wide distribution. Spider mites of the family Tetranychidac such as *Tetranychus urticae, Tetranychus canadensis, Tetranychus cinnabarinus, Tetranychus pacificus, Byrobia practiosa, Oligonychus pratensis, Oligonychus ilicis, Panonychus citri, Panonychus ulmi*, and similar related species, are of particular interest and economic importance. Other economically important mites are those of the family Tarsonemidae, such as *Steneotarsonemus pallidus.*

Compounds of the present invention of the following formulas A and B are effective control agents for spider mites.

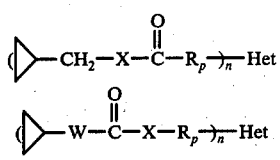

wherein,

X is oxygen or sulfur;
R is alkylene, alkenylene, or alkynylene;
W is —$(CH_2)_m$—, —CH=CH—, —$CH_2$—CH=CH—, —$CH_2$—C≡C—, or —C≡C—;
n is one or two;
p is zero or one;
m is zero or a positive interger from one to four; and
Het is a five or six member heterocyclic ring containing at least one hetero atom (oxygen, nitrogen or sulfur) or a nine to twelve member fused heterocyclic ring system of which at least one ring contains at least one nitrogen, sulfur, or oxygen atom, said heterocyclic ring or heterocyclic ring system optionally substituted by one or more alkyl, alkoxy, aryl, aryloxy, aralkyl, aralkoxy, halogen, or nitro groups.

Hereinafter, each of X, R, W, n, p, m, and Het is as defined above unless otherwise specified.

The compounds of formulas A and B are applied to the mite at any stage, namely, during the egg, larvae, nymphal or adult stages in view of their effect in causing inhibition of egg hatching, abnormal development leading to death, inability to pass from one stage to the next, or inability to reproduce. Some of the compounds also exhibit a residual ovicidal effect. A compound of formula A or B can be applied at dosage levels of the order of 0.001% to 1%. Suitable carrier substances include liquid or solid inert carriers, such as water, acetone, xylene, mineral or vegetable oils, talc, vermiculite, and silica. Treatment of mites in accordance with the present invention can be accomplished by spraying, dusting, or otherwise contacting the mites and/or their eggs or larvae directly or indirectly. Generally, a concentration of less than 25% of active compound is employed, although a higher concentration of the active compound can be used depending on the type of application apparatus. The formulations can include emulsifying agents and wetting agents to assist in the application and effectiveness of the active ingredient.

Preferred compounds of formulas A and B are those wherein n is two, X is oxygen and Het is a five- or six-membered heterocyclic ring optionally substituted by one or more alkyl, aryl, alkoxy, aryloxy, halogen, or nitro.

Particularly preferred are those compounds wherein Het is pyridine, thiophene, or furan and p is zero or R is alkylene of one to six carbon atoms.

The esters and thioesters of this invention can be prepared by conventional esterification methods that are well-known by those skilled in the art.

The esters and thioesters of formula A can be prepared by the reaction of an acid halide of the formula

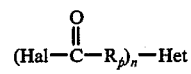

with cyclopropanemethyl alcohol or cyclopropanemethyl hydrosulfide to obtain the corresponding ester or thioester. The reaction is carried out in the presence of pyridine and either neat or in an organic solvent inert to the reaction, such as a hydrocarbon or ether solvent. Usually a molar excess of the alcohol or mercaptan is employed and the reaction proceeds at room temperature satisfactorily, although higher or lower temperatures may be used.

Alternatively, the esters may be prepared by transesterification of a corresponding alkyl ester with the lithium salt of cyclopropanemethyl alcohol in an inert solvent or by esterification with cyclopropanemethyl alcohol and an acid catalyst in an inert solvent.

Cyclopropanemethyl alcohol can be prepared as described by Sarel and Newman, *J. Am. Chem. Soc.* 78, 5416 (1956); Sneen et al, ibid, 83, 4843 (1961); Siegel and Bergstron, ibid 72, 3815 (1950) and 74, 145 (1952); U.S. Pat. Nos. 2,294,084 and 3,074,984; and references cited therein.

The esters and thioesters of formula B can be prepared by the reaction of an acid halide of the formula

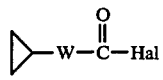

with an alcohol or thiol of the formula (HX—$R_p$)$_n$Het to obtain the corresponding ester or thioester. The reaction is carried out in the presence of pyridine and either neat or in an organic solvent inert to the reaction, such as a hydrocarbon or ether solvent. The reaction proceeds satisfactorily at room temperature, although higher or lower temperatures may be used.

Alternatively, the esters can be prepared by esterification of the acid

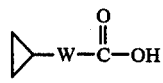

with the alcohol (HO—$R_p\!\!\!\!-\!\!\!)_n$Het and an acid catalyst in an inert solvent.

The acid halides are conveniently prepared by treating the corresponding acid with a halogenating agent such as thionyl chloride, phosphorus pentachloride, or phosphorus tribromide.

Acids of the formula

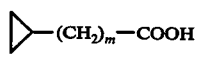

can be prepared from alkyl halides or from cyclopropanemethyl halides. cyclopropanemethyl halides of the formula

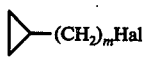

can be prepared by reaction of an alcohol of the formula $H_2C\!=\!CH\!-\!(CH_2)_m\!OH$ and $CH_2I_2$ in the presence of zinc-copper couple. The reaction is carried out in an inert solvent, such as an ether or hydrocarbon solvent, and proceeds satisfactorily with heating to yield

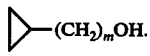

This alcohol intermediate is then converted to the halide with e.g. thionyl chloride in a solvent inert to the reaction and with cooling from −10° to 0° C. The reaction is carried out in the presence of a base such as pyridine or a trialkyl amine.

Cyclopropylmethyl halides (m=1) can also be prepared by treating cyclopropylmethyl alcohol with an aromatic or aliphatic sulfonyl chloride, such as mesyl chloride or tosyl chloride, in pyridine solvent at 0–10° C. The corresponding cyclopropylmethyl sulfonate thus formed is then treated with lithium bromide or lithium chloride in a solvent such as acetone to yield the corresponding cyclopropylmethyl chloride or bromide.

Cyclopropylmethyl chloride can also be prepared by treating cyclopropylmethyl alcohol with thionyl chloride according to the procedure described by Caserio et al., Tetrahedron II, 171 (1960).

The alkyl chloride

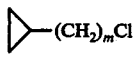

can be conveniently converted to the corresponding acid or acyl halide by reacting it with 1,3-diethiane and n-butyllithium in the presence of N,N,-N',N'-tetramethylethylenediamine. The reaction is chilled to 0° to 10° for from 7 to 21 days and the intermediate

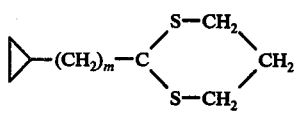

isolated. This intermediate is then treated with boren trifluoride and ether and red mercuric oxide in a solvent inert to the reaction to yield

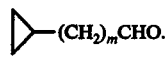

The aldehyde can be oxidized to the acid using $CrO_3$ and sulfuric acid in the presence of acid and water.

The alkyl chloride, except where m is one, can also be treated with magnesium metal and a Grignard initiator in an ether solvent inert to the reaction and then reacted with carbon dioxide to yield the corresponding acid.

The term "alkyl", as used herein, refers to a straight or branched chain aliphatic hydrocarbon group of one to fifteen carbon atoms, e.g., methyl, ethyl, propyl, i-propyl, n-butyl, s-butyl, t-butyl, pentyl, hexyl, heptyl, n-octyl, 2-methyloctyl, nonyl, decyl, undecyl, 2-methylundecyl, 6-methylundecyl, dodecyl, pentadecyl and the like. The term "lower alkyl" refers to an alkyl group of one to six carbon atoms.

The term "aryl", as used herein, refers to a monovalent aromatic hydrocarbon group containing from six to fourteen carbon atoms such as phenyl, tolyl, xylyl, mesityl, naphthyl, ethylphenyl, t-butylphenyl, isopropylphenyl, chlorophenyl, and methoxyphenyl.

The term "aralkyl", as used herein, refers to a monovalent hydrocarbon group containing from 7 to 15 carbon atoms in which a hydrogen atom of an alkyl group having a chain length of one to six carbon atoms is substituted by an aryl group, such as benzyl, phenethyl, methylbenzyl, naphthylmethyl and naphthylethyl.

The terms "aryloxy", "aralkyloxy" and "alkoxy", as used herein, refer to the groups aryl—0°, aralkyl—O— and alkyl—0—respectively, where aryl, aralkyl and alkyl are as defined above.

The term "alkylene" refers to a bivalent methylene, ethylene, or polymethylene moiety, including branched chain polymethylene containing from one to twenty carbon atoms.

The term "alkenylene" refers to a bivalent radical of two to twenty carbon atoms derived by removing two hydrogen atoms from one or more carbon atoms of a branched or unbranched hydrocarbon chain containing one or more sites of olefinic unsaturation.

The term "alkynylene" refers to a bivalent radical of 2 to 20 carbon atoms derived by removing two hydrogen atoms from one or more carbon atoms of a branched or unbranched hydrocarbon chain containing one or more sites of acetylenic unsaturation.

The term "halogen", as used herein, refers to a fluorine, chlorine, bromine or iodine.

The term "Hal", as used herein, refers to chlorine or bromine.

The term "Het", as used herein, refers to the radical formed by the removal of one or two hydrogen atoms from a five or six member heterocyclic ring containing at least one hereto atom (oxygen, nitrogen or sulfur) or to a 9, 10, 11, or 12 member fused heterocyclic ring system containing at least one hetero atom (oxygen, nitrogen, or sulfur). Typical ring systems contemplated for use within the scope of this invention are thiophene, benzo[b]thiophene, furan, pyran, isobenzofuran, chromene, 211-pyrrole, pyrrole, imidazole, pyrazole, pyridine, pyrazine, pyrimidine, pyridazine, indolizine, isoindole, 311-indole, indole, 1H-indazole, purine, 4H-quinolizine, isoquinoline, quinoline, phthalazine, naphthyridine, quinoxaline, quinazoline, cinnoline, isothiazole, isoxazole, furazan, isochroman, chroman, pyrrolidine, pyrroline, imidazolidine, imidazoline, pyrazolidine, pyrazoline, piperidine, piperazine, indoline, isoindoline, morpholine and benzimidazole.

The esters and thioesters of the present invention can be used along or in an inert carrier substance for the control of mites (Acarina) or can be used in mixture with pesticides and/or juvenile hormone analogs known in the art in order to obtain a broader spectrum of activity. Suitable pesticides include Baygon, Captan, Seven, Ciodrin, Systox, Diazinon, Vapona, Cygon, Dimethrin, Dursban, Malathion, Plictran and Parathion. Typical juvenile hormone analogs which can be used in mixture with the compounds of the present invention are described in Belgian Pat. Nos. 778,241 and 778,242.

The esters and thioesters of the present invention are useful for the control of mites and ticks which are ectoparasitic on animals and birds. The compounds can be applied in either solution or in powder (dust) form in a conventional manner.

The following examples are provided to illustrate the synthesis of the esters of the present invention and the practice of the present invention. Temperature in degrees Centigrade.

EXAMPLE 1

To a suspension of 40.0 g. of 3-buten-1-el and 90.8 g. zinc-copper couble in 450 ml. of dry ether under nitrogen at room temperature is added about 15 ml. of diiodomethane. The reaction flask is heated externally with a heat gun until the reaction mixture refluxes by itself (about one hour). When the initial reflux rate begins to subside, 79 ml. of diiodomethane is added dropwise over a period of one-half hour to maintain a constant reflux rate. The reaction mixture is then heated to reflux by means of a water bath at 40°–45°, refluxed for 5 hours, allowed to sit overnight at room temperature and then refluxed for an additional 6 hours.

The reaction is quenched by first cooling the reaction mixture to room temperature and adding saturated ammonium chloride solution until gas evolution ceases and a black precipitate is formed. The reacton mixture is filtered and the solid filtrate washed twice with ether. The ether phase is then washed with a saturated aqueous solution of ammonium chloride, 3N sulfuric acid, 10% sodium bicarbonate, water and brine. The reaction mixture is then filtered, dried over calcium sulfate, filtered through activity III alumina, concentrated at atmospheric pressure, and distilled at reduced pressure to yield 25.8 g. of crude 2-cyclopropaneethyl alcohol.

Using the procedure of this example, 3-cyclopropanepropyl alcohol and 4-cyclopropanebutyl alcohol are prepared from 4-penten-1-ol and 5-hexen-1-ol.

EXAMPLE 2

To a solution of 29.01 g. of 2-cyclopropaneethyl alcohol and 52.3 mls. tributyl amine (specific gravity = 0.778) in 200 mls. of anhydrous ether of 0° under nitrogen is added dropwise 15.8 mls. of thionyl chloride (specific gravity = 1.655). The reaction mixture is stored at −3° for four days and then poured into an ether/water mixture. The water phase is decanted away and the ether phase is washed with 5% sodium hydrogen carbonate, water, and brine and then dried over calcium sulfate, concentrated at atmospheric pressure and distilled at reduced pressure to yield 2-cyclopropaneethyl chloride.

Using the procedure of this example, cyclopropanemethyl chloride, 2-cyclopropaneethyl chloride, 3-cyclopropanepropyl chloride and 4-cyclopropanebutyl chloride are prepared from cyclopropanemethyl alcohol, cyclopropaneethyl alcohol, 3-cyclopropyl alcohol and 4-cyclopropanebutyl alcohol respectively.

EXAMPLE 3

A mixture of 9.9 g. of 2-cyclopropaneethyl chloride, 150 mls. of anhydrous tetrahydrofuran, 2.41 g. of magnesium metal, and 0.87g. of ethylene dibromide is heated to near boiling point for one hour. An additional 0.114 g. magnesium and 0.89 g. of etylene bromide is then added and the reaction mixture is boiled for 4.25 hours at which time most of the magnesium metal has disappeared. Dry carbon dioxide gas is then continuously added over a period of one hour to the reaction mixture which is cooled with a water bath and stirred vigorously during this time. The reaction mixture is stirred overnight at 24° and then ether, water, and 3N sulfuric acid is added. The aqueous phase separated and extracted twice with a one:one mixture of ether and pentane. The combined ether layers are washed with water and brine and then dried over calcium sulfate. The solvent is removed by rotary evaporation to yield 8.11 g. of 3-cyclopropanepropionic acid.

Using the procedure of this example, 4-cyclopropanebutyric acid and 5-cyclopropanevaleric acid are prepared from the corresponding chlorides (except cyclopropanemethyl chloride) prepared in Example 2.

EXAMPLE 4

To a mixture of 23.5 g. of 1,3-dithiane in 500 mls. of anhydrous tetrahydrofuran at −30° under nitrogen is added 133 mls. of 1.51 M n-butyllithium in hexane solution over a period of one-half hour. The reaction mixture is stirred at −30° To −20° for 2 hours, warmed to −10°, and 23.5 g. of cyclopropanemethyl chloride and 15 mls. of N,N,N′,N′-tetramethylethylene diamine in 24 mls. of tetrahydrofuran is added. The reaction mixture is then refrigerated at 3° for 14 days. Ether, pentane, and water are then added and the mixture is acidified with 100 mls. of aqueous 3N sulfuric acid. The aqueous layer is separated and extracted with a mixture of ether and pentane. The combined organic layers are then washed with water and brine, dried over calcium sulfate, and the solvent removed to yield 33.6 g. of a pale yellow product, 2-(cyclopropanemethyl)-1,3-dithiane.

To 230 mls. of aqueous tetrahydrofuran (15% water) is added 38.1 g. of boron trifluoride-ethyl ether, followed by 58 g. of red mercuric oxide. To this mixture is then added dropwise 23.4 g. of 2-(cyclopropanemethyl)-1,3-dithiane in 10 mls. of tetrahydrofuran. The mixture is stirred for five hours and then allowed to remain at 24° overnight. Ether (200 mls.) is added to the mixture and the upper phase decanted, washed twice with potassium carbonate, twice with brine and then dried over calcium sulfate. The mixture is filtered into a 15 cm. Vigreux distillation apparatus and the solvent removed at 42°–73° to yield cyclopropaneacetaldehyde.

EXAMPLE 5

To a mixture of 0.10 g. of cyclopropaneacetaldehyde and 1 ml. of anhydrous acetone is added at 24° enough Jones Reagent (67 g. chromium trioxide, 125 mls. water, 58 mls. concentrated sulfuric acid, water to dissolve salts) to produce a persistent orange color. After 5 minutes, 50 mls. of ether and 10 mls. of water is added, the organic layer is separated and washed twice with 20 ml. portions of aqueous saturated sodium chloride solution and then dried over calcium sulfate. The solvent is removed by rotary evaporation to yield 0.12 g. of pale yellow liquid, 2-cyclopropaneacetic acid.

EXAMPLE 6

To a mixture of 1.14 g. of 3-cyclopropaneprionic acid, 30 mls. of anhydrous ether, and 1.1 mls. of thionyl chloride ($d_{10} = 1.66$), at 24°, is added 0.2 mls. of dimethyl formamide. The mixture is stirred for 45 minutes and then the upper of the two layers is decanted away. Excess thionyl chloride and solvent is removed by rotary evaporation to yield, a pale orange liquid, 3-cyclopropaneproionyl chloride.

Using the procedure of this example, 2-cyclopropaneacetyl chloride, 4-cyclopropanebutyrl chloride, and 5-cyclopropanepentanoyl chloride are prepared from the acids of Examples 3 and 5 and cyclopropanecarbonyl chloride is prepared from cyclopropanecarboxylic acid.

EXAMPLE 7

To a mixture of 3.46 g. of anhydrous sodium hydrosulfide and 14 ml. dimethylformamide is added, with cooling, 4.0 g. of cyclopropanemethyl chloride. After standing two hours at room temperature, water and ether are added, the aqueous phase is separated and extracted with ether, and the combined organic phases are washed with brine, dried over calcium sulfate, filtered and distilled to yield cyclopropanemethyl hydrosulfide, boiling at 97°–98° at 1 atm.

EXAMPLE 8 a. to a mixture of 1800 ml. of anhydrous methylene chloride, 80.5 ml. of anhydrous pyridine, and about 20 g. of barium oxide at room temperature under nitrogen is added 55.0 g. of chromium trioxide over a 5 minute period. The mixture is stirred for one hour and then 7.21 g. of cyclopropanemethyl alcohol is added over a five minute period. The reaction mixture is stirred for one hour and then is poured onto a dry column of 130 g. of Florisil (Floridin Co.). The column is drained and then is washed with 100 ml. of methylene chloride. The eluate is dried over calcium sulfate, filtered into a 40 cm. - Vigreux distillation apparatus and distilled. The fraction distilling at 111°–114° (1 atm.) being further purified by spinning band distillation to yield to fractions boiling at 61°–79° and at 79°–80° that are identified by infrared analysis as mixtures of cyclopropanecarboxaldehyde and pyridine.

b. To a mixture of 2.34 g. of cyclopropanecarboxaldehyde in pyridine (prepared as in (a) above), 19 ml. of anhydrous dimethylformamide and 7.47 g. of triethylphosphonacetate at room temperature under argon is added 1.47 g. of sodium hydroxide pellets. The mixture is surrounded by a room temperature water bath and is stirred overnight. Ether, pentane and water are added and the mixture is acidified to pH2 with 3N sulfuric acid. The aqueous layer is separated and extracted twice with a 1:1 mixture of ether and pentane. The combined organic layers are washed twice with brine and then dried over calcium sulfate. The mixture is filtered and the solvent is removed to yield 2.84 g. of ethyl 3-cyclopropaneacrylate.

c. A mixture of 2.0 g. of ethyl 3-cyclopropaneacrylate, 8 ml. of methanol, 4 ml. of water, and 0.74 g. of sodium hydroxide pellets is boiled for 2 hours. Ether, pentane, water, and brine are added to the mixture which is then acidified with 10 ml. of 3N sulfuric acid. The aqueous layer is separated and extracted twice with a 1:1 mixture of ether and pentane. The combined organic layers are washed with brine, dried over calcium sulfate and the solvent removed to yield 1.11 g. of colorless, crystalline 3-cyclopropaneacrylic acid.

Using the procedure of this example, 4-cyclopropanecrotonic acid can be prepared from cyclopropaneethyl alcohol. 3-Cyclopropaneproprolic acid and 4-cyclopropane-2-butynoic acid are prepared by the reaction of

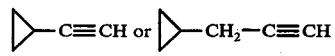

and an alkyl magnesium bromide followed by treatment with carbon dioxide and acidification to yield the desired acid. The starting acetylenic compounds are prepared from cyclopropyl methyl ketone or cyclopropylmethyl methyl ketone using the procedure described by Schoberth and Hanack Communications, Dec. 1972, p. 703 Angew. Chem.

EXAMPLE 9

To a mixture of 3.00 g. of 5-nitro-2-furan-carboxylic acid and 2.06 ml. of thienyl chloride in 50 ml. ether is added 0.45 ml. of dimethyl formamide. The reaction mixture is stirred overnight, under nitrogen, at room temperature. The ether solution is then decanted and the solvent removed to yield 5-nitro-2-furancarboxylic acid chloride, which is then dissolved in 50 ml. ether at 0°. To this solution is added, under nitrogen, 2.06 g. of cyclopropanemethyl alcohol and 3.1 of pyridine. The reaction mixture is allowed to warm to room temperature and is stirred for six days. Ether and water is added to the reaction mixture, the ether layer is decanted, and the aqueous phase is extracted once with ether. The combined organic phases are washed with 2N sulfuric acid, sodium carbonate, water, saturated copper sulfate, and brine, dried over calcium sulfate and the solvent removed to give 3.36 g. of cyclopropanemethyl 5-nitro-2-furancarboxylate, melting point 78°–80°.

Follwing the procedure of Example 9, the esters of Column II are prepared from the acids of Column I and cyclopropanemethyl alcohol.

I 2-furnanacetic acid
4-(2-furyl)butyric acid
benzo[b]thiophene-2-carboxylic acid
2H-pyran-2-carboxylic acid
Δ¹(3H)ᵃ-isobenzofuranaceticacid
1- isobenzofurancarboxylic acid
pyrazinecarboxylic acid
3-isoxazolecarboxylic acid
2-thiopheneacetic acid
5-chloro-2-thiopheneactic acid
4-methyl-2-thiopheneacetic acid
3-nitro-2-thiopheneacetic acid
5-phenyl-2-thiopheneacetic acid
3-thiopheneacetic acid
2,5-dimethyl-3-thiopheneacetic acid
2-methyl-3-thiopheneacetic acid
4-(3-thienyl)butyric acid
4-(2-chloro-4-thienyl)butyric acid
4-(2,5-dimethyl-3-thienyl)butyric acid
2-thiophenecarboxylic acid
3-bromo-2-thiophenecarboxylic acid
4-bromo-5-nitro-2-thiophenecarboxylic acid 4-octyl-5-nitro-2-thiophenecarboxylic acid
4-octyloxy-2-thiophenecarboxylic acid
5-octyloxy-2-thiophenecarboxylic acid
3-t-butoxy-2-thiophenecarboxylic acid
5-chloro-2-thiophenecarboxylic acid
4-methyl-2-thiophenecarboxylic acid
5-isopropyl-2-thiophenecarboxylic acid
5-nitro-2-thiophenecarboxylic acid
5-methoxy-2-thiophenecarboxylic acid
3-phenyl-2-thiophenecarboxylic acid
5-octyl-2-thiophenecarboxylic acid
3-thiophenecarboxylic acid
cyclopropanemethyl 2-furanacetate
cyclopropanemthyl 4-(2-furyl)butyrate
cyclopropanemethyl benzo[b]thiophene-2-carboxylate
cyclopropanemethyl 2-H-pyran-2-carboxylate
cyclopropanemethyl Δ$^1$)3H)$^a$-isobenzofuranacetate
cyclopropanemethyl 1-isobenzofurancarboxylate
cyclopropanemethyl pyrazinecarboxylate
cyclopropanemethyl 3-isoxazolecarboxylate
cyclopropanemethyl 2-thiopheneacetate
cyclopropanemethyl 5-chloro-2-thiopheneacetate
cyclopropanemethyl 4-methyl-2-thiopheneacetate
cyclopropanemethyl 3-nitro-2-thiopheneacetate
cyclopropanemethyl 5-phenyl-2-thiopheneacetate
cyclopropanemethyl 3-thiopheneacetate
cyclopropanemethyl 2,5-dimethyl-3-thiopheneacetate
cyclopropanemethyl 2-methyl-3-thiopheneacetate
cyclopropanemethyl 4-(3-thienyl)butyrate
cyclopropanemethyl 4-(2-chloro-4-thienyl)butyrate
cyclopropanemethyl 4-(2,5-dimethyl-3-thienyl)butyrate
cyclopropanemethyl 2-thiophenecarboxylate
cyclopropanemethyl 3-bromo-2-thiophenecarboxylate
cyclopropanemethyl 4bromo-5-nitro-2-thiophenecarboxylate
cyclopropanemethyl 4-octyl-2-thiophenecarboxylate
cyclopropanemethyl 4-octyloxy-2-thiophenecarboxylate
cyclopropanemethyl 5-octyloxy-2-thiophenecarboxylate
cyclopropanemethyl 3-t-butoxy-2-thiophenecarboxylate
cyclopropanemethyl 5-chloro-2-thiophenecarboxylate
cyclopropanemethyl 4-methyl-2-thiophenecarboxylate
cyclopropanemethyl 5-isopropyl-2-thiophenecarboxylate
cyclopropanemethyl 5-nitro-2-thiophenecarboxylate
cyclopropanemethyl 5-methoxy-2-thiophenecarboxylate
cyclopropanemethyl 3-phenyl-2-thiophenecarboxylate
cyclopropanemethyl 5-octyl-2-thiophenecarboxylate
cyclopropanemethyl 3-thiophenecarboxylate

EXAMPLE 10

To a mixture of 11.07 g. of isonicotinic acid and 15.75 g. of thionyl chloride is added 1.13 g. of dimethylformamide. The suspension is heated to reflux, benzene is added and the reaction mixture is refluxed for one hour. Excess thionyl chloride and benzene is removed and the resultant hydrochloride salt of isonicotinoyl chloride is suspended in 40 ml. of methylene chloride and 21.4 g. of pyridine and 6.48 g. of cyclopropanemethyl alcohol. The reaction mixture is stirred for two days at room temperature. Solid sodium bicarbonate, sodium chloride, and brine are added and the solution is extracted three times with methylene chloride. The methylene chloride is washed with brine, dried over sodium sulfate and distilled to give 13.55 g. of cyclopropylmethyl isonicotinate, boiling point 78°-80° at 0.04 mm.

Following the procedure of Example 10, the esters of Column IV are prepared from the acids of Column III and cyclopropanemethyl alcohol.

III nicotinic acid
1-methylnicotinic acid
5-chloronicotinic acid
2-methylisonicotinic acid

IV cyclopropanemethyl nicotinate
cyclopropanemethyl 1-methylnicotinate
cyclopropanemethyl 5-chloronicotinate
cyclopropanemethyl 2-methylisonicotinate

EXAMPLE 11 a. To a solution of 15 g. of 5-methylfurfural and 30.5 g. of triethylphosphonoacetate in 170 ml. of anhydrous dimethylformamide at room temperature under nitrogen is added 6.0 g. of sodium hydroxide. The reaction mixture is stirred overnight at room temperature and then 300 ml. of a 1:1 ether/pentane mixture is added followed by the addition of 150 ml. of saturated ammonium chloride. The organic layer is removed and the aqueous layer extracted with 200 ml. of 1:1 ether/pentane. The combined organic phases are washed with water and brine, dried over calcium sulfate, and concentrated to yield 21.36 g. of ethyl 3-(5-methyl-2-furyl)acrylate.

b. To a solution of 2.00 g. of cyclopropanemethyl alcohol in 10 ml. anhydrous tetrahydrofuran containing a trace of triphenylmethane at 0° under nitrogen is added enough n-butyllithium to turn the solution red. Cyclopropanemethyl alcohol is then added dropwise until the red color disappears. The reaction mixture is warmed to room temperature and stirred for one-half hour. The solvent is removed by evaporation and 40 ml. of tetrahydrofuran is added to the remaining solid. To this mixture is added at room temperature, under nitrogen, 2.00 g. of ethyl 3-(5-methyl-2-furyl)acrylate, prepared as in a) above. The reaction mixture is stirred for one day at room temperature, and then taken up in a 1:1 mixture of ether/pentane, followed by the addition of 50 ml. of saturated ammonium chloride and 50 ml. of water are added, the organic layer is separated and the aqueous layer extracted with 1:1 ether/pentane. The combined organic phases are washed with saturated ammonium chloride, water, and brine, dried over calcium sulfate, and the solvent removed to yield 2.01 g. of cyclopropanemethyl 3-(5-methyl-2-furyl)acrylate, boiling point 90° (bath) at 0.15 mm.

Following the procedure of Example 10, the esters of Column VI can be prepared from the acids of Column V.

V 3-(2-thienyl)acrylic acid
3-(5-bromo-2-thienyl)acrylic acid
3-(5-chloro-2-thienyl)acrylic acid
3-(5-ethyl-2-thienyl)acrylic acid
3-(5-phenyl-2-thienyl)acrylic acid
3-(3-thienyl)acrylic acid
3-(5-benzimidazolidinyl)propiolic acid

VI cyclopropanemethyl 3-(2-thienyl)acrylate
cyclopropanemethyl 3-(5-bromo-2-thienyl)acrylate
cyclopropanemethyl 3-(5-chloro-2-thienyl)acrylate
cyclopropanemethyl 3-(5-ethyl-2-thienyl)acrylate
cyclopropanemethyl 3-(5-phenyl-2-thienyl)acrylate
cyclopropanemethyl 3-(3-thienyl)acrylate
cyclopropanemethyl 3-(5-benzimidazolidinyl)propiolate

EXAMPLE 12

To a solution of 2.5 g. of 2,5-diiodothiophene in 5 ml. of anhydrous tetrahydrofuran and 5 ml. of anhydrous ether at −5°, under nitrogen, is added dropwise over the period of one-half hour 14.92 ml. of 1.5 M n-butyllithium. After standing for two hours at 0°, carbon dioxide gas is added to the mixture for one-half hour at 0° and one-half hour at 10°. The reaction mixture is stirred at room temperature overnight. Water is added, the aqueous layer is acidified with 2N sulfuric acid, and the solution is then extracted with ether, the combined organic phases are washed with water and brine, dried over calcium sulfate, filtered and the solvent removed to yield 2,5-thiophenedicarboxylic acid (about 60% pure).

EXAMPLE 13 a. To an ether solution of 1.00 g. of 2,5-thiophenedicarboxylic acid (prepared in Example 12 above) and 0.27 ml. of dimethyl formamide at 6°, under nitrogen, is added 1.08 ml. of thionyl chloride. The reaction mixture is allowed to warm to room temperature and then is stirred for one and one half hours. The upper layer of the resultant biphasic solution is removed and the remaining viscous oil is washed with anhydrous hexane and the solvent removed by evaporation to yield 2,5-thiophenedicarboxylic acid chloride.

b. To an ether solution of the 2,5-thiophenedicarboxylic acid chloride, prepared in a) above, at 10° is added 1.09 g. of cyclopropanemethyl alcohol and 1.38 g. of pyridine. The reaction mixture is allowed to warm to room temperature and stirred for 18 hours. Water is then added and the solution is extracted with ether. The organic phase is separated and washed with 2N sulfuric acid, water, aqueous 10% sodium carbonate, water, saturated aqueous copper sulfate, water, and brine. The solution is then dried over calcium sulfate, filtered, and the solvent removed to yield 1.5 g. of dark brown liquid which crystallizes on standing. The product is recrystallized from hexane to yield .45 g. of bis(cyclopropanemethyl)thiophene-2,5-dicarboxylate, melting point 76°–77.5°.

EXAMPLE 14

To a mixture of 188 g. of pyridine-2,5-dicarboxylic acid monohydrate, 1000 ml. of dry ether, 1000 ml. of methylene chloride, and 2.64 ml. of thionyl chloride at 24° is added 11 ml. of dimethylformamide. The biphasic (solid/liquid) mixture is then stirred at 24° overnight. The mixture is then clear, monophasic, and light orange.

To this mixture is added, at a rate sufficient to maintain gentle reflux, 262 g. of cyclopropanemethyl alcohol. After about fifteen minutes following the addition, the mixture is nearly monophasic and clear. The reaction mixture is allowed to stand at room temperature for three days and is then filtered. The filter-cake is washed with 300 ml. of pentane. Since the filtrate is biphasic, the bottom layer is separated and to it is added 1500 ml. of a 1:1 mixture of ether and pentane. The mixture is then made basic with a 20% aqueous potassium hydroxide solution, the organic layer is separated and washed four times with 500 ml. portions of water, and once with 200 ml. of brine and then is dried over calcium sulfate. The removal of solvent by evaporation yields 75.10 g. of crystalline product which is recrystallized from hexane to yield bis(cyclopropanemethyl)pyridine-2,5-dicarboxylate, melting point 66°–67°.

Following the procedure of Example 13 or 14, the esters of Column VIII are prepared from the acids of Column VII and cyclopropanemethyl alcohol.

VII 3,4-bis(p-chlorophenyl)-2,5-thiophenedicarboxylic acid
3,4-bis(p-methoxyphenyl)-2,5-thiophenedicarboxylic acid
3,4-dimethyl-2,5-thiophenedicarboxylic acid
3,4-diphenyl-2,5-thiophenedicarboxylic acid
3-phenyl-2,5-thiophenedicarboxylic acid
3,4-thiophenedicarboxylic acid
2,5-diphenyl-2,4-thiophenedicarboxylic acid
2-phenyl-3,4-thiophenedicarboxylic acid
2-methyl-3,4-thiophenedicarboxylic acid
2-methyl-5-phenyl-3,4-thiophenedicarboxylic acid
2,5-thiophenedipropionic acid
3,5-pyridinedicarboxylic acid
1,3-pyridinedicarboxylic acid
2,3-pyridinedicarboxylic acid
2,4-pyridinedicarboxylic acid
2,6-pyridinedicarboxylic acid
2,5-pyridinedicarboxylic acid
3,6-dimethyl-2,5-pyridinedicarboxylic acid
4,6-diphenyl-2,5-pyridinedicarboxylic acid
2,5-pyridinediacrylic acid
2,5-pyridinedibutyric acid
2,3-furandiacetic acid
2,5-furandiacrylic acid
2,3-furandicarboxylic acid
4-isobutyryl-2,3-furandicarboxylic acid
5-phenyl-2,3-furandicarboxylic acid
2,5-furandicarboxylic acid
3,4-furandicarboxylic acid
2-benzyl-3,4-furandicarboxylic acid
2-butoxy-3,4-furandicarboxylic acid
2,5-diethyl-3,4-furandicarboxylic acid
3,4-furandipropionic acid
benzo[b]thiophene-2,3-dicarboxylic acid
2H-pyran-4,6-dicarboxylic acid
2H-pyran-2,6-dicarboxylic acid
4,4-dichloro-2H-pyran-2,6-dicarboxylic acid
2H-pyran-3,5-dicarboxylic acid
1,4-isobenzofurandioctanoic acid
1,7-isobenzofurandioctanoic acid
pyrazine-2,3-dicarboxylic acid
pyrazine-2,5-dicarboxylic acid
3,6-dimethyl-pyrazine-2,5-dicarboxylic acid
isoxazole-3,4-dicarboxylic acid
isoxazole-3,5-dicarboxylic acid
isoxazole-3,5-dipropionic acid
1,3-benzimidazolinedicarboxylic acid
1,3-benzimidazolinedipropionic acid

VIII bis(cyclopropanemethyl) 3,4-bis(p-chlorophenyl)thiophene-2,5-dicarboxylate bis(cyclopropanemethyl) 3,4-bis(p-methoxyphenyl)thiophene-2,5-dicarboxylate
bis(cyclopropanemethyl) 3,4-dimethylthiophene-2,5-dicarboxylate
bis(cyclopropanemethyl) 3,4-diphenylthiophene-2,5-dicarboxylate
bis(cyclopropanemethyl) 3-phenylthiophene-2,5-dicarboxylate
bis(cyclopropanemethyl) thiophene-3,4-dicarboxylate
bis(cyclopropanemethyl) 2,5-diphenylthiophene-3,4-dicarboxylate
bis(cyclopropanemethyl) 2-phenylthiophene-3,4-dicarboxylate
bis(cyclopropanemethyl) 2-methylthiophene-3,4-dicarboxylate
bis(cyclopropanemethyl) 2-methyl-5-phenylthiophene-3,4-dicarboxylate
bis(cyclopropanemethyl) thiophene-2,5-dipropionate
bis(cyclopropanemethyl) pyridine-3,5-dicarboxylate
bis(cyclopropanemethyl) pyridine-1,3-dicarboxylate
bis(cyclopropanemethyl) pyridine-2,3-dicarboxylate
bis(cyclopropanemethyl) pyridine-2,4-dicarboxylate
bis(cyclopropanemethyl) pyridine-2,6-dicarboxylate
bis(cyclopropanemethyl) pyridine-2,5-dicarboxylate
bis(cyclopropanemethyl) 3,6-dimethylpyridine-2,5-dicarboxylate
bis(cyclopropanemethyl) 4,6-diphenylpyridine-2,5-dicarboxylate
bis(cyclopropanemethyl) pyridine-2,5-diacrylate
bis(cyclopropanemethyl) pyridine-2,5-dibutyrate
bis(cyclopropanemethyl) furan-2,3-diacetate
bis(cyclopropanemethyl) furan-2,5-diacrylate
bis(cyclopropanemethyl) furan-2,3-dicarboxylate
bis(cyclopropanemethyl) 4-isobutyrylfuran-2,3-dicarboxylate
bis(cyclopropanemethyl) 5-phenylfuran-2,3-dicarboxylate
bis(cyclopropanemethyl) furan-2,5-dicarboxylate
bis(cyclopropanemethyl) furan-3,4-dicarboxylate
bis(cyclopropanemethyl) 2-benzylfuran-3,4-dicarboxylate
bis(cyclopropanemethyl) 2-butoxyfuran-3,4-dicarboxylate
bis(cyclopropanemethyl) 2,5-diethylfuran-3,4-dicarboxylate
bis(cyclopropanemethyl) furan-3,4-dipropionate
bis(cyclopropanemethyl) benzo[b]thiophene-2,3-dicarboxylate
bis(cyclopropanemethyl) 2H-pyran-4,6-dicarboxylate
bis(cyclopropanemethyl) 2H-pyran-2,6-dicarboxylate
bis(cyclopropanemethyl) 4,4-dichloropyran-2,6-dicarboxylate
bis(cyclopropanemethyl) 2H-pyran-3,5-dicarboxylate
bis(cyclopropanemethyl) isobenzofuran-1,4-dioctanoate
bis(cyclopropanemethyl) isobenzofuran-1,7-dioctanoate
2,3-bis(cyclopropanemethyl) pyrazinedicarboxylate
2,5-bis(cyclopropanemethyl) pyrazinedicarboxylate
2,5-bis(cyclopropanemethyl) 3,6-dimethyl-pyrazinedicarboxylate
3,4-bis(cyclopropanemethyl) isoxazoledicarboxylate
3,5-bis(cyclopropanemethyl) isoxazoledicarboxylate
3,5-bis(cyclopropanemethyl) isoxazoledipropionate
1,3-bis(cyclopropanemethyl) benzimidazolinedicarboxylate
1,3-bis(cyclopropanemethyl) benzimidazolinedipropionate Thioesters of Formula A are prepared by treating a solution of the corresponding acid or diacid in benzene with oxalyl chloride, heating for one to eight hours and then removing the benzene solvent. To this concentrate is added an inert solvent and respectively at least a one-fold or two-fold molar excess of the cyclopropanemethyl mercaptan prepared in Example 7 followed at 0° by at least a one-fold or two-fold excess of pyridine. The reaction mixture is stirred and the product separated by pouring the mixture into water, adding ether, separating the organic phase, washing with aqueous sodium bicarbonate and brine, drying over calcium sulfate and removing the solvent.

In the above manner, the acids and diacids of Column IX are converted to the thioesters of Column X.

IX 5-nitro-2-furancarboxylic acid
2-furanacetic acid
4-(2-furyl)butyric acid
benzo[b]thiophene-2-carboxylic acid
pyrazinecarboxylic acid
3-isoxazolecarboxylic acid
2-thiopheneacetic acid
3-nitro-2-thiophenacetic acid
3-thiophenecarboxylic acid
nicotinic acid
3-(5-methyl-2-furyl)acrylic acid
3-(2-thienyl)acrylic acid
5-benzimidazolinepropiolic acid
2,5-thiophenedicarboxylic acid
2,5-thiophenedipropionic acid
2,5-pyridinedicarboxylic acid
2,5-furandiacrylic acid
2,3-furandiacetic acid
2,5-furandicarboxylic acid
2H-pyran-4,6-dicarboxylic acid
isoxazole-3,5-dicarboxylic acid

X

S-cyclopropanemethyl 5-nitro-2-furanthioate
S-cyclopropanemethyl 2-furanethanethioate
S-cyclopropanemethyl 2-furanbutanethioate
S-cyclopropanemethyl benzo[b]thiophene-2-thioate
S-cyclopropanemethyl pyrazinethioate
S-cyclopropanemethyl 3-isoxazolethioate
S-cyclopropanemethyl 2-thiopheneethanethioate
S-cyclopropanemethyl 3-nitro-2-thiopheneethanethioate
S-cyclopropanemethyl 3-thiophenethioate
S-cyclopropanemethyl nicotinethioate
S-cyclopropanemethyl 3-(5-methyl-2-furyl)propenethioate
S-cyclopropanemethyl 2-thiophenepropenethioate
S-cyclopropanemethyl 5-benzimidazolinethiopropiolate
bis(S-cyclopropanemethyl) thiophene-2,5-dithioate
bis(S-cyclopropanemethyl) thiophene-2,5-dipropionthioate
bis(S-cyclopropanementhyl) pyridine-2,5-dithioate bb
bis(S-cyclopropanemethyl) furan-2,5-propenedithioate
bis(S-cyclopropanemethyl) furan-2,3-dithioacetate
bis(S-cyclopropanemethyl) furan-2,5-dithioate
bis(S-cyclopropanemethyl) 2H-pyran-4,6-dithioate
bis(S-cyclopropanemethyl) isoxazole-3,5-dithioate

EXAMPLE 15

To a solution of 5.20 g. of cyclopropanecarboxylic acid chloride and 4.15 g. of pyridine in 50 ml. of tetrahydrofuran is added dropwise a solution of 6.85 g. of 3-(3-pyridyl)-1-propanol in 15 ml. of tetrahydrofuran. After standing for one hour, solid sodium bicarbonate is added and the reaction mixture is diluted with 250 ml. of water. The organic material is extracted with chloroform and distilled to yield 7.53 g. of 3-(3-pyridyl)propyl cyclopropanecarboxylate, boiling point 109°–111° at 0.06 mm.

Heterocyclic alcohols and thioalcohols can be conveniently prepared from the corresponding acids or diacids by reduction with e.g. lithium aluminum hydride and, if the thiol is desired, treatment with sodium hydrosulfide using the procedure of Example 7.

Following the procedure of Example 15, the esters of Column XII are prepared from at least one or two molar equivalants, respectively of the acid chlorides of the corresponding acids of Examples 6 and 8 and the alcohols, thiols, diols and dithiols of Column XI.

XI 2,5-thiophenedimethanol
2,3-thiophenedimethanol
2,6-pyridinedimethanol
2,5-pyridinediol
3,5-pyridinediol
3,4-furandiethanol
3,4-furandimethanol
benzo[b]thiophene-4,7-diol
2H-pyran-2,2-dimethanol
pyrazine-2,5-diol
pyrazineethanol
2-furanmethanol
3-furanmethanol

XII 2,5-bis(cyclopropanecarbonyloxymethylene)thiophene
2,3-bis(cyclopropanecarbonyloxymethylene)thiophene
2,6-bis(cyclopropanecarbonyloxymethylene)pyridine
2,6-bis(cyclopropanecarbonyloxyethylene)pyridine
2,5-bis(cyclopropanecarbonyloxy)pyridine
3,5-bis(cyclopropanecarbonyloxy)pyridine
3,4-bis(cyclopropanecarbonyloxyethylene)furan
3,4-bis(cyclopropanecarbonyloxymethylene)furan
4,7-bis(cyclopropanecarbonyloxy)benzo[b]thiophene
2,2-bis(cyclopropanecarbonyloxymethylene)-2H-pyran
2,5-bis(cyclopropanecarbonyloxy)pyrazine
cyclopropanecarbonyloxyethylenepyrazine
2-furanmethyl cyclopropanecarboxylate
3-furanmethyl cyclopropanecarboxylate

EXAMPLE 16

The acid chloride of the acids under Column XIII is reacted with cyclopropanemethyl alcohol to prepare the respective ester under Column XIV using the procedures of Example 13 or 14.

XIII 4,7-benzo[b]thiophenedicarboxylic acid
1,3-isobenzofurandicarboxylic acid
2,5-pyrroledicarboxylic acid
2,4-imidazoledicarboxylic acid
4,7-indoledicarboxylic acid
1,4-isoquinolinedicarboxylic acid
5,8-quinolinedicarboxylic acid
3,5-isothiazoledicarboxylic acid
2,6-piperidinedicarboxylic acid
4,7-benzimidazoledicarboxylic acid

XIV 4,7-bis(cyclopropanemethyl)benzo[b]thiophenedicarboxylate
1,3-bis(cyclopropanemethyl)isobenzofurandicarboxylate
2,5-bis(cyclopropanemethyl)pyrroledicarboxylate
2,4-bis(cyclopropanemethyl)imidazoledicarboxylate
4,7-bis(cyclopropanemethyl)indoledicarboxylate
1,4-bis(cyclopropanemethyl)isoquinolinedicarboxylate
5,8-bis(cyclopropanemethyl)quinolinedicarboxylate
3,5-bis(cyclopropanemethyl)isothiazoledicarboxylate
2,6-bis(cyclopropanemethyl)piperidinedicarboxylate
4,7-bis(cyclopropanemethyl)benzimidazoledicarboxylate

EXAMPLE 17

Following the procedures of Examples 13 or 14, the esters under Column XVI are prepared from the acids under Column XV.

XV 2,4-thiophenedicarboxylic acid
2,4-benzo[b]thiophenedicarboxylic acid
2,4-furandicarboxylic acid
1,4-isobenzofurandicarboxylic acid
2,4-pyrroledicarboxylic acid
4,5-imidazoledicarboxylic acid
2,4-indoledicarboxylic acid
5,8-isoquinolinedicarboxylic acid
2,5-quinolinedicarboxylic acid
3,4-isothiazoledicarboxylic acid
2,5-piperidinedicarboxylic acid
4,6-benzimidazoledicarboxylic acid

XVI 2,4-bis(cyclopropanemethyl)thiophenedicarboxylate
2,4-bis(cyclopropanemethyl)benzo[b]thiophenedicarboxylate
2,4-bis(cyclopropanemethyl)furandicarboxylate
1,4-bis(cyclopropanemethyl)isobenzofurandicarboxylate
2,4-bis(cyclopropanemethyl)pyrroledicarboxylate
4,5-bis(cyclopropanemethyl)imidazoledicarboxylate
2,4-bis(cyclopropanemethyl)indoledicarboxylate
5,8-bis(cyclopropanemethyl)isoquinolinedicarboxylate
2,5-bis(cyclopropanemethyl)quinolinedicarboxylate
3,4-bis(cyclopropanemethyl)isothiazoledicarboxylate
2,5-bis(cyclopropanemethyl)piperidinedicarboxylate
4,6-bis(cyclopropanemethyl)benzimidazoledicarboxylate

EXAMPLE 18

Following the procedures of Examples 13 or 14, the esters under Column XVIII are prepared from the acids under Column XVII.

XVII 3,7-benzo[b]thiophenedicarboxylic acid
3,7-isobenzofurandicarboxylic acid
3,4-pyrroledicarboxylic acid
2,5-imidazoledicarboxylic acid
3,7-indoledicarboxylic acid
1,5-isoquinolinedicarboxylic acid
3,8-quinolinedicarboxylic acid 3,5-piperidinedicarboxylic acid
5,6-benzimidazoledicarboxylic acid

XVIII 3,7-bis(cyclopropanemethyl)benzo[b]thiophenedicarboxylate
3,7-bis(cyclopropanemethyl)isobenzofurandicarboxylate
3,4-bis(cyclopropanemethyl)pyrroledicarboxylate
2,5-bis(cyclopropanemethyl)imidazoledicarboxylate
3,7-bis(cyclopropanemethyl)indoledicarboxylate
1,5-bis(cyclopropanemethyl)isoquinolinedicarboxylate
3,8-bis(cyclopropanemethyl)quinolinedicarboxylate
3,5-bis(cyclopropanemethyl)piperidinedicarboxylate
5,6-bis(cyclopropanemethyl)benzimidazoledicarboxylate

What is claimed is:
1. The compound, bis(cyclopropanemethyl)2,6-pyridinedicarboxylate.
2. The compound, bis(cyclopropanemethyl)2,5-pyridinedicarboxylate.

* * * * *